United States Patent [19]

Smoot et al.

[11] Patent Number: 4,690,760
[45] Date of Patent: Sep. 1, 1987

[54] NOVEL CARTRIDGE WITH STRESS RELIEVING MEMBER

[75] Inventors: Michael A. Smoot, Oakmont; Herbert W. Barch, Natrona Heights; Balbhadra Das, Allison Park, all of Pa.

[73] Assignee: PPG Industries, Inc., Pittsburgh, Pa.

[21] Appl. No.: 860,394

[22] Filed: May 7, 1986

Related U.S. Application Data

[63] Continuation-in-part of Ser. No. 637,233, Aug. 28, 1984, abandoned.

[51] Int. Cl.[4] .............................................. B01D 13/01
[52] U.S. Cl. ............................... 210/321.5; 210/321.1; 210/433.2; 210/494.3
[58] Field of Search ............... 210/321.1, 321.2, 321.3, 210/321.4, 321.5, 433.2, 494.1, 494.3, 323.2; 55/158; 422/48

[56] References Cited

U.S. PATENT DOCUMENTS

| | | | |
|---|---|---|---|
| 2,106,744 | 2/1938 | Hood et al. | 106/36.1 |
| 2,334,961 | 11/1943 | Schoenlaub | 106/50 |
| 2,571,074 | 10/1951 | Tiede et al. | 106/50 |
| 3,268,313 | 8/1966 | Burgman et al. | 65/5 |
| 3,397,790 | 8/1968 | Newby et al. | 210/321 |
| 3,510,393 | 5/1970 | Burgman et al. | 161/178 |
| 3,630,700 | 12/1971 | Hammel | 65/21 |
| 3,650,721 | 3/1972 | Hammel et al. | 106/31 |
| 3,690,465 | 9/1972 | McGinnis | 210/321.1 |
| 3,847,626 | 11/1974 | Erickson et al. | 106/50 |
| 4,042,359 | 8/1977 | Schnabel et al. | 65/2 |
| 4,045,851 | 9/1977 | Ashare et al. | 29/157 R |
| 4,061,574 | 12/1977 | Clark | 210/321 R |
| 4,166,747 | 9/1979 | Neely, Jr. | 106/50 |
| 4,172,794 | 10/1979 | Sigdell | 210/232 |
| 4,358,377 | 11/1982 | Clark | 210/323.2 |
| 4,368,124 | 1/1983 | Brumfield | 210/321.3 |
| 4,610,789 | 9/1986 | Barch | 210/321.4 |

OTHER PUBLICATIONS

"Microporous Glass For Reverse Osmosis", by P. W. McMillan et al., Dept. pf Physics, Univ. of Warwick, Coventry, UK, pp. 1187–1199.

Primary Examiner—Ernest G. Therkorn
Attorney, Agent, or Firm—John E. Curley

[57] ABSTRACT

A fluid separation device in the form of a cartridge is shown in which there is provided a fluid inlet to the cartridge, a distribution tube to feed fluid from the center of the cartridge outwardly across alternate layers of permeable membranes and glass fibers, rovings and strands and wherein the fibers are porous, hollow, or porous and hollow. The fibers are oriented parallel to each other and sealed at one end of the cartridge and open at the other end when hollow fibers are used. A vessel for housing the cartridge is also shown.

21 Claims, 5 Drawing Figures

NOVEL CARTRIDGE WITH STRESS RELIEVING MEMBER

This application is a continuation-in-part of Ser. No. 637,233, filed Aug. 2, 1984, now abandoned.

BACKGROUND OF THE INVENTION

In many filtration processes today membranes are utilized to filter various components of fluid systems. For example, membranes are used to separate gas components from each other in gaseous streams containing multiple gases, to separate various dissolved components in liquid solutions from each other and to selectively permit certain ions in a solution to pass across a membrane while blocking others. Membranes are also utilized to a great extent to immobilize proteins, enzymes and cells. The enzymes, so immobilized are used as catalysts to increase reaction rates or to convert materials in solution from one form to another. Membranes are also utilized in various applications today to trap or immobilize living cells within a substrate forming the membrane.

In general, membranes of various types have been employed for these purposes. In the electrolysis field, for example, polymer sheet membranes which are selectively permeable to alkali metal ions are utilized. Porous glass beads have also been employed in many processes for the purpose of immobilizing enzymes for use in other chemical processes. Organic fibers have also been utilized in many applications, for example, the dialysis of blood. These organic fibers have been utilized both in the hollow and porous state where the material to be purified, in this case blood, is passed through a hollow organic fiber and is purified by enriching it in oxygen and depleting it of waste materials through the pores.

Inorganic materials are particularly interesting for membrane applications since they are, generally speaking, inert and depending on composition, alkali or acid resistant. These properties render such inorganic materials useful in purification systems that are acidic or alkaline. Further, their inertness renders such inorganic materials useful in cell, protein and enzyme immobilization since they are non-reactive to these substances and also to contaminants such as microorganisms that might be present in solutions being treated. Inorganic substances further can be readily cleaned without suffering severe damage during cleaning and sterilization, whereas many organic substances cannot be cleaned using normal cleaning materials such as calcium hypochlorite solutions. Interest in inorganic substrates in the form of hollow glasses which are porous is demonstrated by an article in "The Journal of Material Science" (11), 1976 at pages 1187-1199 by P. W. McMillan and C. E. Matthews. The recent U.S. Pat. No. 4,042,359 also shows a device made of porous glass tubes. These devices use individual tubes in what appears to be limited capacity reactors since the tubes are separated from each other with each tube restrained at each end. A need, therefore, exists for inorganic substrates that can be effectively utilized in reverse osmosis, ultrafiltration, enzyme, protein and cell immobilization and other like processes in a commercial reactor to provide a large number of porous glass fibers for use in the process being conducted.

Applicants, by virtue of the instant invention, have supplied this need by providing novel fiber glass containing cartridges and reactors which can be effectively utilized for separation and immobilization procedures. The separation or immobilization units (hereinafter referred to as reactors) can be tailored for ultrafiltration, reverse osmosis and microfiltration, as well as for for enzyme, protein and cell immobilization. The cartridges and reactors are compact and designed to carry large quantities of glass fibers in a small cross-sectional area. They are also easily adapted to cleaning and the cartridges can be treated prior to insertion in a reactor to provide fibers having the desired physical characteristics for the particular use to which they will be put.

SUMMARY OF THE INVENTION

In accordance with one embodiment of the instant invention, a cartridge or module is provided which comprises a fluid distribution tube, preferably having a fluid permeable membrane surrounding it. A layer of glass fibers, glass fiber strands or glass fiber rovings is placed over the fluid permeable membrane in the preferred embodiment, or the distribution tube itself, with the fibers, strands or roving being oriented in parallel with the long axis of the fluid distribution tube. A second layer of fluid permeable material is placed over the fibers, strands or rovings. The cartridge is completed by continuing to place alternate layers of fibers, strands or rovings and layers of fluid permeable materials until the desired numbers of fibers, strands or rovings are in place with the outer layer of the cartridge, preferably being a fluid permeable material. The fibers, strands or rovings and the fluid permeable layers are attached to the distribution tube by casting the upper and lower ends of them in a suitable castable material such as a catalytic or thermoset curable resin to thereby form a unitary module or cartridge. Interspaced between the upper casting and the outer surface of the distributor tube is a stress relieving member which permits the upper end cap of the casting to readily move on the surface of the distributor tube should the fibers contract or expand.

In a further embodiment of the invention, a fluid separation or immobilization reactor is provided which generally comprises an enclosed vessel having a top, bottom and sidewalls. Means are provided to introduce fluid to the vessel and means are also provided to remove fluid therefrom.

A cartridge of the first mentioned embodiment, hereinabove referred to, is positioned in the vessel. Means to pass fluid from the exterior of the vessel to the interior of the cartridge are also provided. The vessel is further provided with sealing means at the cover and means are provided to seal the cartridge to the vessel wall at the end of the cartridge remote from the fluid introduction means.

The various embodiments of the inventions will be apparent to one having ordinary skill in the art from consideration of the ensuing description and claims.

BRIEF DESCRIPTION OF THE DRAWINGS

For a more complete understanding of the instant invention, reference is made to the accompanying drawings in which.

DETAILED DESCRIPTION OF THE DRAWINGS

Figure 1:
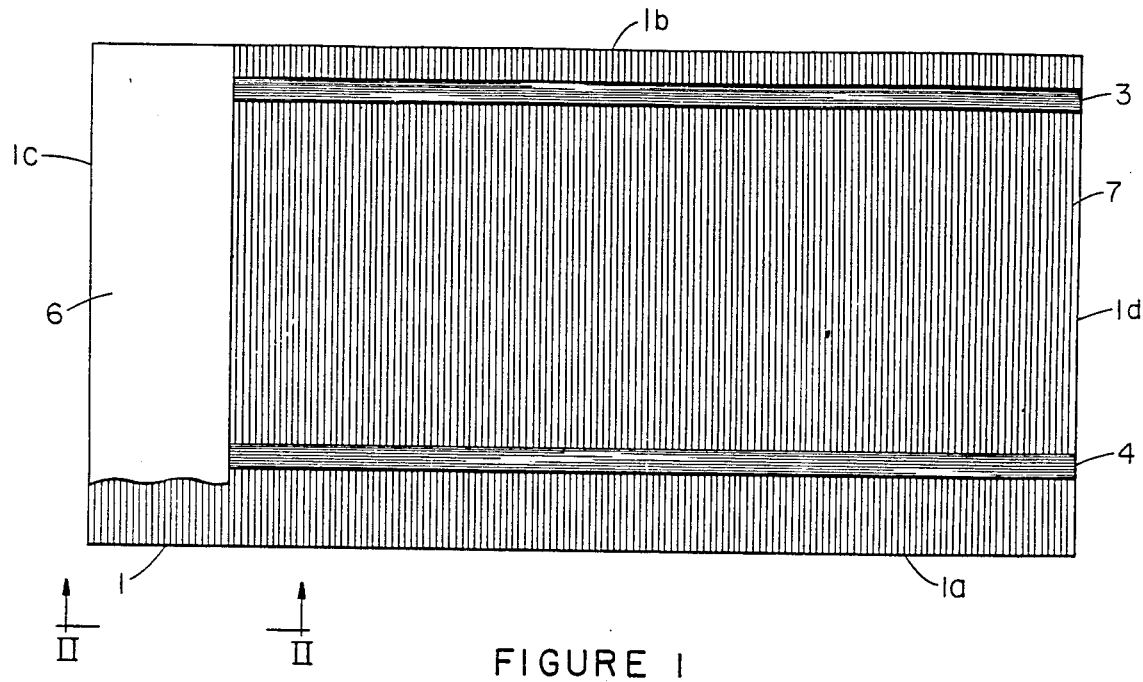
FIG. 1 is a plan view of a mat structure suitable for use in the instant invention.

Turning now to the drawings and to FIG. 1 and FIG. 2 in particular, the invention will be described as it applies to an embodiment in which strands of glass fibers are used to form a mat to be used in a cartridge and reactor of the instant invention. It will be understood that the fibers used in the strands are made of glass. While in this embodiment, the fibers are hollow, they can be porous only or porous and hollow or a combination of all these forms or two of the three forms and still fall within the scope of the invention. Similarly, while strands of hollow glass fibers are used in the drawing, the mat shown can be made of individual fibers or rovings as well as the strands shown or a combination of two or more of the group of fibers, strands and rovings.

Figure 3:
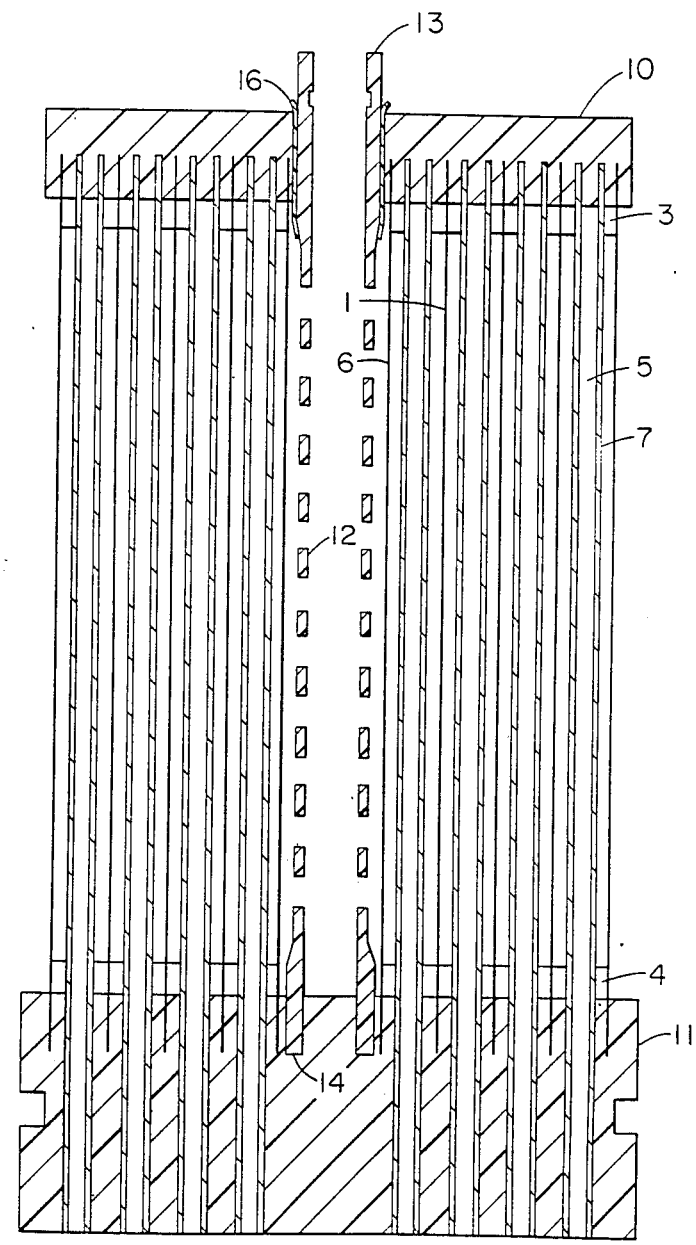
FIG. 3 is a diagrammatic illustration of the cartridge of the instant invention.

In FIG. 1, there is shown a flat, fluid permeable sheet 1 on which are positioned a plurality of hollow glass fiber strands 7 which are fixed to the surface of the permeable sheet 1 and which are in parallel alignment with each other and edges 1c and 1d of the permeable sheet 1. Extending longitudinally along the permeable sheet 1 and parallel to edges 1a and 1b thereof are two adhesive strips or ribbons 3 and 4. Strips or ribbons 3 and 4 are formed of an adhesive material which is of sufficient depth and width to cohesively bond the strands 7 to one another to keep them in parallel alignment. The strips 3 and 4 also prevent resin wicking into the fibers during casting of the mats into cartridge form as shown in FIG. 3. The ribbons 3 and 4 also bond the strands 7 to the permeable sheet 1.

Figure 2:
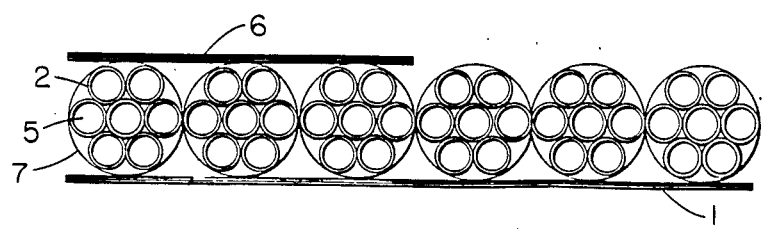
FIG. 2 is a cross-section of the mat of FIG. 1 taken along lines II—II.

FIG. 2 is an enlarged view of a cross-section of FIG. 1 taken along line II—II showing the hollow fibers 2 which make up the strands 7. The fibers 2 as shown have a lumen 5 which runs the length of the fibers 2. As illustrated in the drawing, since strands 7 are employed on the surface of permeable sheet 1, a plurality of hollow fibers 2 (seven in the illustration) are arranged in parallel in each of the strands 7. Also shown in FIG. 2 is the inclusion of a second fluid permeable sheet 6, which is of a short width and overlays the first several rows of strands 7 affixed to the permeable membrane 1. The purpose of the permeable sheet 6 is to provide a permeable membrane at one end of the mat so that it can be utilized in a cartridge for use in a filtration or dialysis system through which fluid is introduced through a distributor tube. The sheet 6 protects the first layer of strands from damage by dissipating fluid flow forces entering the mat when it is wrapped around a fluid distributor in the cartridge of the instant invention.

Fluid permeable sheet as used herein is intended to mean any form of structure such as woven or nonwoven mats, cloth, paper and the like, which are pervious to fluid flow through their surfaces, whether the fluid is liquid or gaseous, and which are resistant to attack by the fluid to which they are subjected. Materials such as fiber glass filament mats, and papers, polyester fiber mats, woven or knitted cloth made of synthetic fibers, glass, cotton and the like can be used. The important consideration for the selection of the material used as the fluid permeable sheet is that it be constructed so that it will support the fibers, strands and rovings to which it is attached and permit free fluid flow through it. The major purposes of the sheet are to protect the fibers, strands and rovings from damage caused by fluid flow forces and by abrasion with each other and surfaces around which the mats of the invention may be wrapped or pressed against in service.

Materials that can be utilized as the ribbons 3 and 4 may consist of hot melt thermoplastic resins or thermoset resins. Some examples of hot melt thermoplastics would be homopolymers or copolymers of polyvinyl acetate, acrylates, acrylonitriles, polysulfones, polyamides and the like. Examples of some thermosets that may be employed are anhydride or amine curable epoxy resins, peroxide curable polyesters, polyimides, and various copolymers of these polymers. These polymers may be dissolved in some solvent and may be contained in a tube with the catalyst. This catalyst can be activated in the presence of heat, oxygen, water or various environments of this nature.

The hollow fibers utilized in the mat of FIGS. 1–4 are glass fibers which have been prepared in such a manner that they are provided with a lumen from one end of the fiber to the other end so that fluid can flow from one end of the fiber to the other end of the fiber unimpeded. A convenient method of preparing hollow fibers is described in assignee's issued U.S. Pat. 3,268,313. Fibers so produced for use in this invention have outside diameters in the range of 5 to 70 microns, preferably 8 to 40 microns. The internal diameters of fibers in the above range of outside diameters is between 2 to 65 microns, and preferably in the range of 4 to 35 microns. Using fibers in this range of diameters large surface area membranes suitable for use in immobilization systems for cell enzyme and protein immobilization are readily obtained. Particular glass fibers that can be used are described in U.S. Pat. No. 3,510,393.

The glass composition forming the fibers, as far as the instant invention is concerned, is not of paramount importance and any glass composition suitable for use in making glass fibers which can be drawn into hollow structures as described in the aforesaid U.S. patents is suitable. Typical glasses which may be employed for this purpose are "E" or "621" glasses and/or other borosilicate glasses containing from 8 to 28 percent $B_2O_3$ on a weight basis of the glass composition. Glasses of these types are described in U.S. Pat. No. 2,106,744; 2,334,961; 2,571,074; 3,650,721. Glasses having low $B_2O_3$ such as described in U.S. Pat. No. 4,166,747 as well as glasses not containing either fluorine or boron such as described in U.S. Pat. No. 3,847,626 and Applicants' assignee's application Ser. No. 562,945, filed Dec. 19, 1983, now abandoned may also be employed.

In those instances, where porous fibers are employed, the porosity is provided to the glass fibers by employing any of many well known techniques to the skilled art. Thus, in treating borosilicate glass, the glass is typically heat treated for a given period of time after which it is treated with a mineral acid to leach out the borosilicate rich phase to provide pores of specific diameter. This system is described in Assignees' U.S. Pat. No. 3,630,700 in connection with glass particles, but the system also applies to treatments involving glass fibers. Assignees' U.S. Pat. No. 3,650,721 shows a system of treating fibers of a boron containing glass which renders them porous using a similar heat treatment followed by an acid leach. Similar treatments to provide porosity to glass fibers are also described in U.S. Pat. No. 4,042,359. In utilizing the principles described in these patents, glass fibers which are solid or hollow can be treated to provide porosity to the fibers. In the case of hollow fibers, where it is desired, the leaching is normally conducted for a sufficient time to provide pores that communicate with the lumen of the hollow fibers. The treatment of fibers to render them porous can be conducted while the fibers are in fiber, strand or roving form or can be conducted while the fibers, strands and rovings are in mat form. It is preferred by Applicants to render fibers porous after they are in mat form and most preferably after they are in a cartridge form such as shown in FIG. 3.

Figure 4:
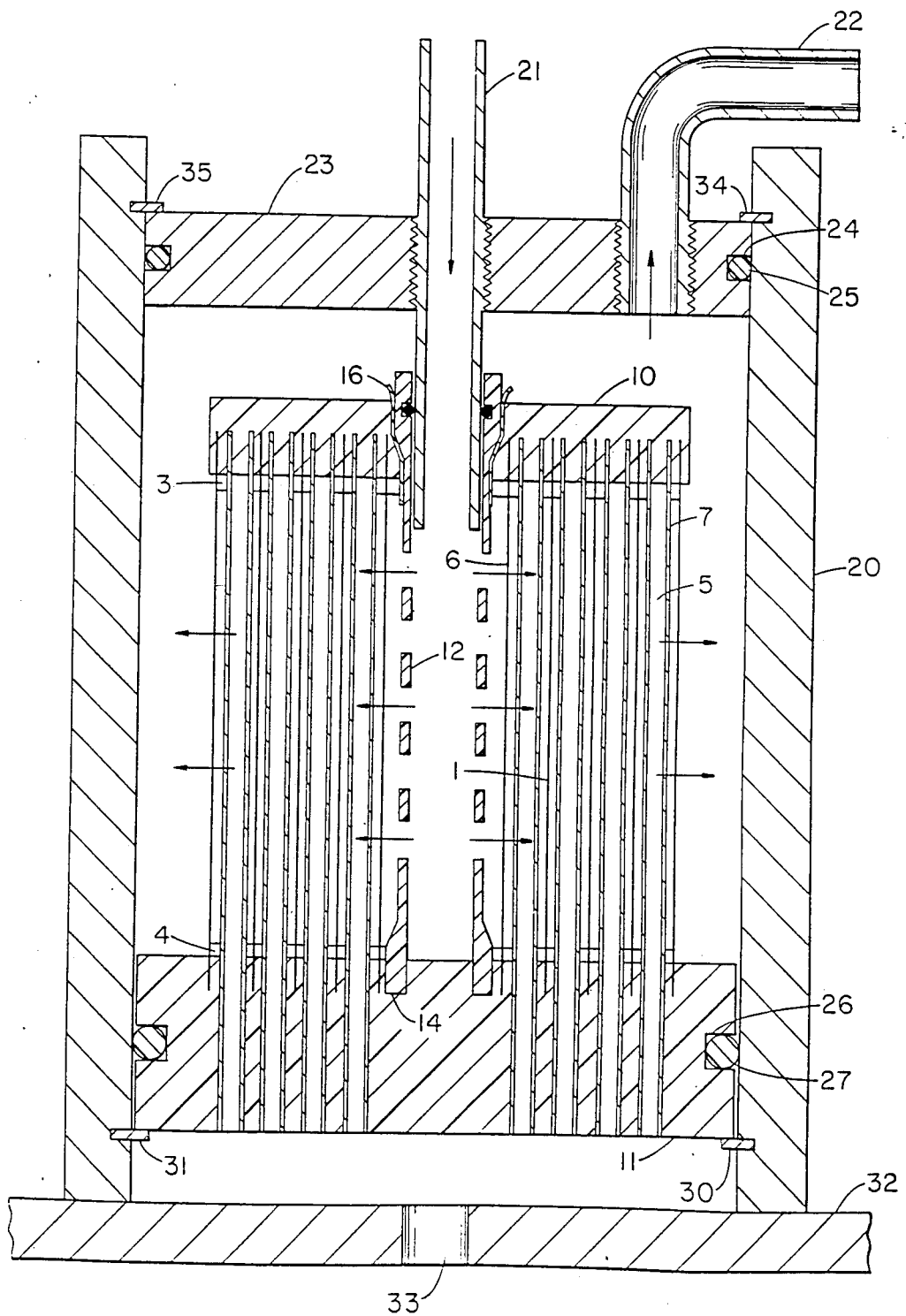
FIG. 4 is a diagrammatic illustration of a reactor of the instant invention with the cartridge of FIG. 3 in place.

Turning to FIG. 3, which depicts the cartridge of the instant invention, an assembly of the mat of FIG. 1 is shown in which the hollow strands 7 are aligned vertically in a catridge that may be used in a fluid separation system. The cartridge involves an upper casing member 10 in which the strands 7 and the fluid permeable sheets 1 and 6 are cast. The adhesive barrier 3 is located just below the casing member 10. Similarly, the hollow strands 7 are also shown cast in a lower casing member 11 and the adhesive barrier 4 is positioned just above the casing member 11. This barrier 4 serves to prevent wicking of resin into the fibers during the casting of member 11. The lumen 5 shown is for illustrative purposes, it being understood that this represents the lumen of each fiber contained in strands 7. The fluid permeable sheet 6 is wrapped around a distributor tube, generally indicated as 12, that runs in a generally centrally disposed relationship to the hollow strands 7 contained in the cartridge and terminates in the casting 10 forming the top of the cartridge. The other end 14 of the distributor tube 12 is embedded in the bottom casing 11. As can be readily seen from the drawing, the first membrane 6 is wrapped completely around the distributor tube 12 and is followed by a layer of hollow strands 7 and then alternate layers of the sheet 1 and the hollow strands 7 as the mat is wrapped in successive wraps around distributor tube 12. A thin plastic sheet 16 is provided around collar 13 at the top of the cartridge. This sheet 16 encompasses the outer surface of the distributor tube 12 located in the upper cap member or casting 10 and extends below cap 10. This sheet or membrane 16 permits cap 10 to move on the tube 12 downwardly in response to shrinkage of the hollow fibers 7 caused, for example, by leaching to render them porous as hereinafter described. By providing this stress relieving member 16, the cap member or casting 10 will automatically move downwardly should strands 7 change in length as by shrinking and thus it prevents the fibers in strands 7 from breaking under such stress caused by a change in fiber length.

operation in which a fluid separation is being conducted, the novel fluid separation device of FIG. 4 is utilized. The fluid separation device of FIG. 4 involves a tubular casing 20 which has a fluid inlet 21, a fluid outlet line 22 and a cover member 23 associated therewith. Cover member 23 is sealed with respect to the sidewalls of the casing 20 utilizing grooves 24 and appropriate gasketing 0 rings 25 at the top. On the bottom, the cartridge itself has a groove 26 associated therewith in which is placed an 0 ring 27 to seal the bottom casing of the cartridge to the walls separation unit. In the embodiment shown, the fibers forming the strands 7 are porous as well as being hollow and fluid is fed through inlet 21 into the distributor tube 12 and passes, as shown by the arrows, through the openings 28 in the distributor tube 12 and through the walls of the fibers in porous hollow strands 7. The material passing through walls of the fibers contained in the strands 7 passes through the lumen 5 of the hollow fibers contained in strands 7 and exits at the end of the resin member 11. The collar 14 of the distributor tube 12 is embedded in member 11 so that fluid entering line 21 must exit through the openings 28 in order to be removed from the system. Fluid that does not pass down through the lumen 5 of the hollow fibers in strands 7 passes to the outside of the cartridge containing the strands 7 and passes between the wall of the casing 20 and the outside of the strands 7 forming the cartridge and upwardly into the feed return duct 22 and out of the system.

In preparing porous glass fibers for use in the cartridges of the instant invention, recourse to several methods may be had. If the glass fibers, strands or rovings in the mat are made of an "E" or "621" glass composition, the mat may be used in a cartridge such as shown in FIG. 1. In this instance, the cartridge may be placed in a unit such as shown in FIG. 4. The inlet tube 21 is capped and the exit 33 is plugged. The vessel 20 is filled to the cap 10 area with 3 N HCl and maintained in the vessel for 0.5 to 5 hours at 40° to 95° C. The vessel 20 is then emptied, flushed with distilled water and is ready for use. It is an important consideration that the plastic film 16 be present around the collar of distributor tube 12 during leaching the glass strands 7 since they tend to shrink during treatment. This film, which may be thin Mylar ® or other plastic materials such as polyethylene, polypropylene, polyethylene terephthalate, Teflon ® and the like, permits cap 10 to move downwardly as the strands 7 shrink to thereby minimize any fracturing of the strands caused by changes in fiber length as they shrink.

In another method using an "E" or "621" glass composition, the mat is used in cartridge form such as FIG. 3 and placed in a vessel such as FIG. 4. In this method, the mat is leached by passing the leaching acid, typically 3 N HCl, into inlet tube 21 and removing it through outlet 22. In the alternative, the leaching acid can be passed into the vessel through line 22 and removed through line 21. This circulating acid is typically fed for 0.5 to 5 hours at temperatures of 40° to 95° C.

In instances where high boron containing glasses are to be employed, the mats are heat treated to phase separate the glass. This is done by subjecting the mat to temperatures of 200° to 750° C. in an oven for a period of time sufficient to form silica rich and borosilicate rich phases in the glass. This can be done from 5 minutes to as long as 24 hours. Since the adhesive may not withstand the oven temperatures, it may be necessary to reapply the adhesive ribbons 3 and 4 before leaching the phase separated mat. Preferably, after the mat is phase separated, it is formed into a cartridge such as FIG. 3 and placed in a reactor similar to FIG. 4. Once the mat is in place in a vessel such as FIG. 4, it may then be leached by the methods above described for the "E" and "621" glasses.

In the alternative, the fiber strands or rovings can be heat treated before forming them into mats and subsequently formed into mats.

The acids used are typically inorganic mineral acids such as HCl, $H_2SO_4$ and $HNO_3$ at normalities of 1 to 6. Strong organic acids such as citric acid may also be used but mineral acids are preferred.

If desired, the mats of "E" or "621" glasses as well as the phase separated borosilicate glasses may be leached by exposing them to the acid treatment in the mat form rather than in cartridge form so long as they are treated for the times and temperatures indicated for the cartridge treatments.

The following is an example of the method used to construct a mat similar to FIG. 1 of hollow glass fibers in roving form.

EXAMPLE 1

A mat similar to that shown in FIG. 1 was prepared as follows:

Hollow fiber glass strands prepared by the process of U.S. Pat. No. 3,268,313 and contained in a roving package are wound onto a drum. The drum used was manufactured by C. A. Litzler Co. of Cleveland, Ohio. It is 48 inches wide and has a 48 inch diameter. Prior to winding, a clear polypropylene sheet is taped to the drum surface. This prevents the adhesive, which is applied later, from sticking to the winder. A 10 mil, fluid permeable, polyester surface mat (Dupont's Reemay ®) is taped to the drum winder, over the polypropylene sheet. The porous polyester mat forms the support backing for the yet to be wound glass roving. A roving containing E-glass fibers with 2% epoxy compatible sizing on the fibers is used to supply fibers for a mat. The roving consists of 40 strands, each strand containing 102 individual hollow fibers whose dimensions are approximately 12 microns O.D. and 6 microns I.D.

The roving is wound onto the drum and results in 14 rovings per inch, or 560 strands per inch or 57,120 fibers per inch. The roving is continuously wound onto the drum with the rovings generally parallel to each other until the drum is covered. The mat resulting is measured and marked at 13 inch sections on the drum. Each mat section will come from the 13 inch ×44 inch pieces (2 inches are lost at each end of the drum). Prior to cutting the mat and removing it from the drum, the adhesive strips 3 and 4 are applied. In this instance, a contact cement manufactured by Franklin Chemical of Columbus, Ohio is used.

Two ½ inch adhesive lines are applied to each mat section. One line is one inch from the end, the other is 2½ inches from the other end. The adhesive lines run perpendicular to the fiber direction and serve to both bond the fibers together and to the polyester fluid permeable sheet as well as serving later to prevent resin wicking. Once the adhesive has dried, the blanket is cut at one of the mat locations. This permits removal of the blanket from the drum winder. The blanket is laid onto a cutting table, and a 13 inch ×22 inch hollow fiber mat is cut to the appropriate length. Using this procedure, a mat is provided which, when used in a 2" diameter module or cartridge such as shown in FIG. 3, has available for use in that cartridge, 370,486 hollow fibers.

EXAMPLE 2

A cartridge similar to FIG. 3 is prepared as follows: A fluid permeable membrane, in this case, a Reemay ® polyester sheet is wrapped around the distributor tube which is a glass fiber reinforced polyester resin tube 12½ inches in length with 8 to 9 inches of the tube length being perforated for fluid flow. The mat of FIG. 1 with the glass fiber side facing the permeable sheet is then rolled onto the distributor tube to provide alternate layers of glass strands and fluid permeable membrane until the entire mat is in place with the outside layer being the permeable sheet. A Mylar ® film is wrapped around the mat and taped in place to keep the mat from unrolling during handling. A 50/50 weight percent mixture of Koppers 1060-5 polyester resin and calcium carbonate is prepared with a Lightnin mixer by combining the ingredients and mixing them for one minute with 1.5 milliliters of Hi-Point 90 catalyst from Witco Chemical Co. A 2" diameter mold with a die having a center pin and four ⅛" depression spaced equidistant around the base of the center pin is employed. The resin mixture is poured into the mold to a depth of ⅛ inch above the floor of the die. The center tube of the cartridge is placed on the pin and lowered onto the die and mold. The resin is allowed to cure. Upon completion of the cure of the first stage casting, the cartridge is removed from the mold and has four ⅛" feet on the bottom.

A resin mixture is then prepared using 200 grams of an epoxy resin, (Epon 828 from Shell Corporation), 170 grams of a polyamide resin (Hy 906 manufactured by Ciba-Geigy), 41.2 grams of $CaCO_3$ filler and 1.2 grams of DY 062 accelerator (manufactured by Ciba-Geigy). The two resins and the filler are heated to about 130° F. The resins are then mixed together using a Lightnin mixer for about 5 minutes. A paste is then made with the $CaCO_3$ and a small quantity of the resin mixture. The remaining resin is then added and all ingredients including the accelerator are mixed together for 5 minutes.

The mold which is a flat bottom cylinder 2" in height and 2" in diameter with a ⅛" shoulder around its interior and spaced 1" from the mold bottom is heated to 200° F. The resin is maintained at 130° F.

The container holding the resin is placed in a vacuum chamber and a vacuum of 27 inches of Hg pulled for 15 minutes. The resin container is then removed. The cartridge and mold are placed in a vacuum chamber and a vacuum of 27 inches is pulled for 10 minutes.

A feed tube is placed in the resin container and coupled to a valve in the vacuum chamber holding the cartridge and mold. The valve communicates with a tube that is positioned above the mold cavity and the resin is evacuated into the mold chamber to the fill line of the mold. Upon filling the mold to the fill line, the mold and cartridge are removed from the chamber and are oven cured at 200° F. for 2 hours and then for 4 hours at 300° F. After cure, the first stage casting is cut away to expose the hollow fibers and the surface is cleaned by abrasion to remove loose particles and fibers.

The cartridge is then inverted and the other end is placed in a mold with a flat bottom which is 1.75 inches in diameter and 1.25 inches high. The cartridge is held in place 13/16 inch from the bottom of the mold and a 50/50 weight percent mixture of Epon 828 and Versamid 140 (manufactured by Henkel Corporation) is poured into the mold and cured at 200° F. for 6 hours. This seals the ends of the fibers and forms the cartridge top.

EXAMPLE 3

Figure 5:
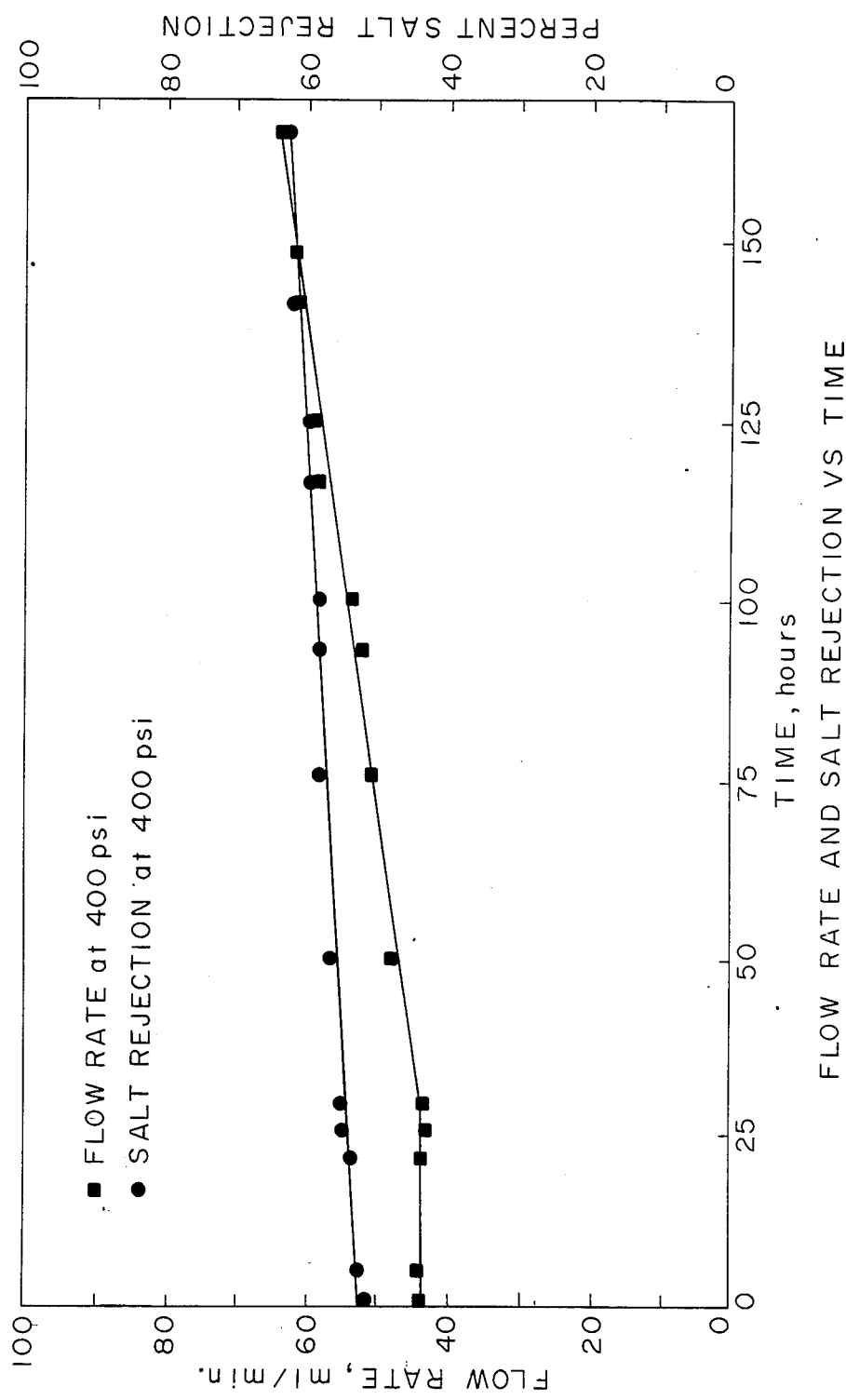
FIG. 5 is a table showing the flow rates and salt rejection vs time based on results obtained in Example 3.

A cartridge of the configuration shown in FIG. 3 prepared as described in Example 2 was placed in a pressure vessel of a type such as shown in shown in FIG. 4 and made of a cast acrylic resin. The module was leached in 3 N HCl at 50° C. for 1 hour by continuously passing the acid through tube 21, across the strands 7 and out tube 22. After 1 hour of leaching, the module was rinsed with distilled water. A 0.5% NaCl solution was passed through the leached module for a period of time in excess of 150 hours and the salt rejection and flow rates of the system were measured. The results are shown in Table 1 shown in FIG. 5.

EXAMPLE 4

A cartridge of the configuration shown in FIG. 3 was prepared as described in Example 2 and was placed in a reactor of the type depicted in FIG. 4. The module was then leached with 3 N HCl at 50° C. for 1 hour using the same procedure as Example 3. The module was then rinsed with distilled water and tested for salt rejection using a concentration of 0.5 and 3.0 percent NaCl in H$_2$O at various pressures. The pressures employed and the results of the salt rejection and flow rates are shown in Table 2.

TABLE II
EFFECT OF SALT CONCENTRATION ON SALT REJECTION AND FLOW RATE

Salt Rejection, % / Flow Rate, ml/min.

| PRESSURE | 0% | | | 0.5% | | | 3.0% | | |
|---|---|---|---|---|---|---|---|---|---|
| Module Number | 1 | 2 | 3 | 1 | 2 | 3 | 1 | 2 | 3 |
| 400 PSI | •/29.5 | •/31.5 | •/28.0 | 65.0/29.0 | 56.2/28.0 | 57.5/27.5 | 32.6/22.0 | 27.9/21.5 | 30.2/20.0 |
| 300 PSI | •/23.0 | •/23.0 | •/21.0 | 62.5/20.5 | 53.7/20.5 | 53.7/19.5 | 29.6/16.0 | 25.6/16.0 | 25.3/15.0 |
| 200 PSI | •/15.5 | •/15.5 | •/14.5 | 56.2/13.0 | 46.2/13.5 | 47.5/13.0 | 20.9/10.0 | 18.6/10.5 | 18.6/9.5 |
| 100 PSI | •/7.5 | •/8.0 | •/7.0 | 47.5/5.5 | 33.7/6.0 | 33.7/6.0 | 13.9/4.5 | 11.6/5.0 | 11.6/4.0 |
| 50 PSI | •/• | •/• | •/• | 18.7/1.5 | 13.7/1.7 | 20.0/1.7 | 7.0/1.2 | 7.0/1.4 | 7.0/1.5 |

As will be readily appreciated, the mats, cartridges and reactors of the instant invention provide a useful separation system for a variety of fluid systems with a large number of fibers available for filtration. In similar fashion, the cartridges and reactors can be utilized to trap enzymes, cell and proteins in the pores of glass centered in the modules.

While the invention has been described with reference to certain specific embodiments and illustrative examples, it is not intended to be limited thereby, except insofar as appears in the accompanying claims.

We claim:

1. A cartridge suitable for use in a fluid separation system comprising a solid, top member having an opening therein, a fluid distributor tube having one end extending through said opening and extending along an axis of said cartridge, said distributor tube having a plurality of openings along its length and having another end embedded in a solid, bottom member sealing it therein, a mat of fluid permeable sheet having a plurality of glass fibers affixed thereto positioned around said distributor tube in successive wraps to provide alternate layers of fluid permeable sheets and glass fibers from the distributor tube to the outside of the cartridge, said glass fibers being oriented in parallel to the distributor tube and to each other and wherein the fibers are embedded in said top member below its upper surface and in said bottom member, said fibers being opened to the atmosphere at the lower surface of said bottom member, means positioned around said distributor tube in the said opening in said top member and surrounding said distributor tube in said opening to thereby provide a sliding surface on which the said top member may move downwardly on said tube in response to changes in the length of the said fibers caused by shrinkage thereof during operation.

2. The cartridge of claim 1 wherein the glass fibers are rovings.

3. The cartridge of claim 2 wherein the glass fibers are hollow.

4. The cartridge of claim 2 wherein the glass fibers are porous.

5. The cartridge of claim 2 wherein the glass fibers are hollow and porous.

6. The cartridge of claim 1 wherein the glass fibers are hollow.

7. The cartridge of claim 1 wherein the glass fibers are porous.

8. The cartridge of claim 1 wherein the glass fibers are hollow and porous.

9. The cartridge of claim 1 wherein the glass fibers are strands.

10. The cartridge of claim 9 wherein the glass fibers are porous.

11. The cartridge of claim 9 wherein the glass fibers are hollow.

12. The cartridge of claim 9 wherein the glass fibers are hollow and porous.

13. A fluid separation device comprising a pressure vessel having a top, a bottom and sidewalls, means to introduce fluid into said vessel, at least one means to remove fluid from said vessel, a cartridge positioned inside said vessel and spaced from the walls thereof, said cartridge having a solid top member with an opening therein, a fluid distributor tube having an end thereof extending through said opening and along an axis of said cartridge, and in fluid communication with said fluid introduction means, said distributor having a plurality of openings along its length and having its other end embedded in a solid bottom member in a sealing relationship, means positioned in said opening around said distributor tube and between said top and said distributor tube to permit said top to move downwardly on said distributor tube, successive layers of fluid permeable sheet and parallel glass fibers positioned around said distributor tube, the glass fibers being parallel to the axis of said cartridge and to each other, said glass fibers being embedded in said top member below the upper surface thereof and being embedded in said bottom member and terminating on the outer surface thereof, and means to seal said cartridge to the vessel sidewalls.

14. The separation device of claim 13 wherein the glass fibers are rovings.

15. The separation device of claim 14 wherein the glass fibers are porous.

16. The separation device of claim 14 wherein the glass fibers are hollow.

17. The separation device of claim 14 wherein the glass fibers are hollow and porous.

18. The separation device of claim 13 wherein the glass fibers are strands.

19. The separation device of claim 18 wherein the glass fibers are porous.

20. The separation device of claim 18 wherein the glass fibers are hollow.

21. The separation device of claim 18 wherein the glass fibers are hollow and porous.